US00PP21063P2

(12) United States Plant Patent
Heuger

(10) Patent No.: US PP21,063 P2
(45) Date of Patent: Jun. 8, 2010

(54) ***HELLEBORUS* PLANT NAMED 'COSEH 710'**
(50) Latin Name: ***Helleborus niger*×*Helleborus lividus***
Varietal Denomination: COSEH 710

(76) Inventor: Josef Heuger, Postfach 11 03, D-49215 Glandorf (DE)

( * ) Notice: Subject to any disclaimer, the term of this patent is extended or adjusted under 35 U.S.C. 154(b) by 0 days.

(21) Appl. No.: 12/319,424

(22) Filed: Jan. 7, 2009

(51) Int. Cl.
*A01H 5/00* (2006.01)

(52) U.S. Cl. ..... Plt./439

(58) Field of Classification Search ..... Plt./439
See application file for complete search history.

*Primary Examiner*—June Hwu
(74) *Attorney, Agent, or Firm*—C. A. Whealy

(57) ABSTRACT

A new and distinct cultivar of *Helleborus* plant named 'COSEH 710', characterized by its upright, outwardly spreading and mounded plant habit; dark green-colored leaves; freely flowering habit; long flowering period; and large light green-colored flowers with reddish pink overtones.

1 Drawing Sheet

Botanical designation: *Helleborus niger*×*Helleborus lividus.*

Cultivar denomination: 'COSEH 710'.

BACKGROUND OF THE INVENTION

The present invention relates to a new and distinct cultivar of *Helleborus* plant, botanically known as *Helleborus niger*× *Helleborus lividus,* and hereinafter referred to by the name 'COSEH 710'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in January, 2003 of an unnamed proprietary seedling selection of *Helleborus niger*, not patented, as the female, or seed, parent with an unnamed proprietary seedling selection of *Helleborus lividus*, not patented, as the male, or seed, parent. The new *Helleborus* plant was discovered and selected by the Inventor as a single flowering plant from within the progeny of the stated cross-pollination grown in a controlled greenhouse environment in Glandorf, Germany in March, 2006.

Asexual reproduction of the new *Helleborus* plant by divisions in a controlled greenhouse environment in Glandorf, Germany since March, 2006, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'COSEH 710'. These characteristics in combination distinguish 'COSEH 710' as a new and distinct cultivar of *Helleborus:*

1. Upright, outwardly spreading and mounded plant habit.
2. Dark green-colored leaves.

3. Freely flowering habit.
4. Long flowering period.
5. Large light green-colored flowers with reddish pink overtones.

Compared to plants of the parent selections, plants of the new *Helleborus* are more uniform and more freely flowering.

Plants of the new *Helleborus* can be compared to plants of *Helleborus niger*×*Helleborus sternii* 'HGC Silvermoon', disclosed in U.S. Plant Pat. No. 15,639. Plants of the new *Helleborus* differ primarily from plants of 'HGC Silvermoon' in the following characteristics:

1. Plants of the new *Helleborus* are more vigorous than plants of 'HGC Silvermoon'.
2. Plants of the new *Helleborus* and 'HGC Silvermoon' differ in leaf and flower color.

BRIEF DESCRIPTION OF THE PHOTOGRAPH

The accompanying colored photograph illustrates the overall appearance of the new *Helleborus* plant, showing the colors as true as it is reasonably possible to obtain in colored reproductions of this type. Colors in the photograph may differ slightly from the color values cited in the detailed botanical description which accurately describe the colors of the new *Helleborus* plant.

The photograph comprises a side perspective view of a typical flowering plant of 'COSEH 710' grown in a container.

DETAILED BOTANICAL DESCRIPTION

The aforementioned photograph and following observations, measurements and values describe plants grown in Glandorf, Germany in 15-cm containers during the winter in an outdoor nursery and under conditions which closely approximate commercial *Helleborus* production. During the production of the plants, day temperatures ranged from 5° C. to 32° C. and night temperatures ranged from 1° C. to 25° C. Plants had been growing for one year when the photograph and the description were taken. In the following description, color references are made to The Royal Horticultural Society Colour Chart, 2007 Edition, except where general terms of ordinary dictionary significance are used.

Botanical classification: *Helleborus niger*×*Helleborus lividus* 'COSEH 710'.

Parentage:

*Female, or seed, parent.*—Unnamed proprietary seedling selection of *Helleborus niger*, not patented.

*Male, or pollen, parent.*—Unnamed proprietary seedling selection of *Helleborus lividus*, not patented.

Propagation:

*Type.*—By divisions.

*Time to initiate roots.*—About 56 days at 4° C. to 12° C.

*Time to produce a rooted young plant.*—About six months at 4° C. to 12° C.

*Root description.*—Thick to thin, fleshy; white to brown in color.

*Rooting habit.*—Sparse.

Plant description:

*Plant form and growth habit.*—Herbaceous perennial; upright, outwardly spreading and mounded plant habit; vigorous growth habit.

*Plant height.*—About 30 cm to 35 cm.

*Plant diameter* (*area of spread*).—About 50 cm to 60 cm.

Foliage description:

*Arrangement.*—Palmately compound with five leaflets per leaf.

*Leaflet length.*—About 7 cm to 14 cm.

*Leaflet width.*—About 2.5 cm to 6 cm.

*Leaflet shape.*—Roughly ovate.

*Leaflet apex.*—Acute.

*Leaflet base.*—Asymmetrically acute.

*Leaflet margin.*—Serrate.

*Leaflet texture, upper and lower surfaces.*—Smooth, glabrous; leathery.

*Leaflet venation pattern.*—Pinnate; reticulate.

*Leaflet color.*—Developing leaves, upper surface: Close to 146A. Developing leaves, lower surface: Close to N199A. Fully developed leaves, upper surface: Close to 147A; venation, close to 146B. Fully developed leaves, lower surface: Close to 191A; venation, close to 187A.

*Petiole.*—Length: About 5 mm to 15 mm. Diameter: About 3 mm to 4 mm. Texture, upper and lower surfaces: Smooth, glabrous. Color, upper and lower surfaces: Close to 200B.

Flower description:

*Flower shape and habit.*—Single rotate flowers; freely flowering habit, about 15 to 25 flowers developing per plant. Petals not observed.

*Fragrance.*—Moderately fragrant, pleasant.

*Natural flowering season.*—Long flowering period; plants flower from December to March in Germany.

*Flower longevity on the plant.*—About three weeks; flowers persistent.

*Flower buds.*—Length: About 1.5 cm to 3 cm. Diameter: About 8 mm to 18 mm. Shape: Ovoid. Color: Close to 145C to 145D.

*Flowers.*—Diameter: About 8 cm. Depth (height): About 2 cm to 3 cm.

*Sepals.*—Arrangement: About five in a single whorl. Length: About 4 cm. Width: About 4 cm. Shape: Broadly ovate to rounded. Apex: Rounded. Base: Obtuse. Margin: Entire. Texture, upper and lower surfaces: Smooth, glabrous; satiny. Color: When opening, upper surface: Close to 145A, flushed with close to 51C. When opening, lower surface: Close to 145A, flushed with close to 51C. Fully opened, upper surface: Close to 144B flushed with close to 51C; color becoming closer to 146B flushed with close to 51C with development. Fully opened, lower surface: Close to 144B flushed with close to 51C.

*Peduncles.*—Strength: Strong. Length: About 25 cm to 30 cm. Diameter: About 5 mm to 10 mm. Aspect: Mostly upright. Texture: Smooth, glabrous. Color: Close to 145B; random spots, close to 187B.

*Reproductive organs.*—Stamens: Quantity per flower: About 70. Anther shape: Elliptical. Anther length: About 1 mm to 2 mm. Anther color: Close to 6D. Pollen amount: None observed. Pistils: Quantity per flower: About five. Pistil length: About 1.5 cm. Stigma shape: Pointed. Stigma color: Close to 145D. Style length: About 1 cm. Style color: Close to 145C to 145D. Ovary color: Close to 145C to 145D. Nectaries: Quantity per flower: About ten. Length: About 1 cm. Shape: Salverform. Color: Towards the base, close to 144B to 144C; towards the apex, close to 151B. Seeds/fruits: Seed and fruit development have not been observed.

Garden performance: Plants of the new *Helleborus* have been observed to have good garden performance and to tolerate rain, wind and temperatures from about −10° C. to about 36° C.

Pathogen/pest resistance: Plants of the new *Helleborus* have not been shown to be resistant to pathogens and pests common to *Helleborus*.

It is claimed:

1. A new and distinct *Helleborus* plant named 'COSEH 710' as illustrated and described.

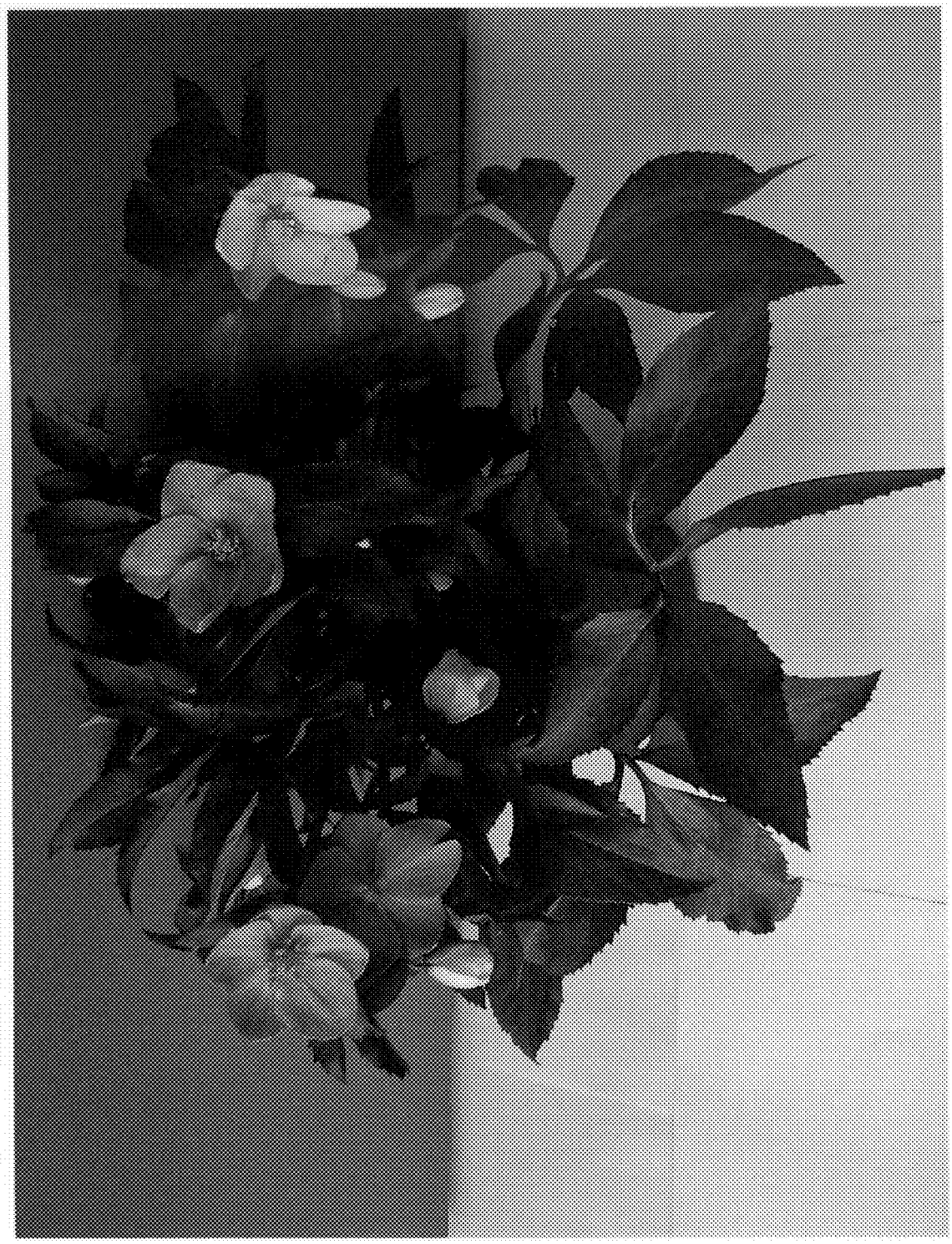

* * * * *